United States Patent [19]

Khadem et al.

[11] Patent Number: 5,552,452
[45] Date of Patent: Sep. 3, 1996

[54] ORGANIC TISSUE GLUE FOR CLOSURE OF WOUNDS

[75] Inventors: John Khadem, Chicago, Ill.; Toan V. Truong, Anaheim Hills, Calif.

[73] Assignee: Arch Development Corp., Chicago, Ill.

[21] Appl. No.: 33,314

[22] Filed: Mar. 15, 1993

[51] Int. Cl.$^6$ .................. C09J 189/00; C09J 189/04; C09J 189/06; C08F 2/50
[52] U.S. Cl. ................... 522/63; 522/84; 522/87; 522/904; 522/2; 523/106; 523/111; 523/113
[58] Field of Search ................. 522/87, 63, 904, 522/2, 84; 523/106, 111, 113

[56] References Cited

U.S. PATENT DOCUMENTS

| 4,039,413 | 8/1977 | Kraemer et al. | 522/87 |
|---|---|---|---|
| 4,057,535 | 11/1977 | Lipatova et al. | 260/77.5 |
| 4,414,976 | 11/1983 | Schwartz et al. | 128/334 R |
| 4,627,879 | 12/1986 | Rose et al. | 106/124 |
| 4,672,969 | 6/1987 | Dew | 128/397 |
| 4,804,691 | 2/1989 | English et al. | 523/118 |
| 4,854,320 | 8/1989 | Dew et al. | 128/397 |
| 4,928,603 | 5/1990 | Rose | 106/124 |
| 5,002,051 | 3/1991 | Dew et al. | 128/395 |
| 5,071,417 | 12/1991 | Sinofsky | 606/8 |
| 5,140,984 | 8/1992 | Dew et al. | 128/395 |
| 5,173,295 | 12/1992 | Wehling et al. | 424/94.67 |
| 5,173,301 | 12/1992 | Itoh et al. | 424/448 |
| 5,219,895 | 6/1993 | Kelman et al. | 522/87 |

FOREIGN PATENT DOCUMENTS

| 0330344 | 8/1989 | European Pat. Off. . |
|---|---|---|
| WO9109641 | 7/1991 | WIPO . |
| WO9202238 | 2/1992 | WIPO . |

OTHER PUBLICATIONS

Andley, Usha P., "Spectroscopic Studies on the Riboflavin-–Sensitized Conformational Changes of Calf Lens α–Crystallin," *Exp. Eye Res.*, 46: 531–544, 1988.

Andley and Clark, "Accessibilities of the Sulfhydryl Groups of Native and Photoxidized Lens Crystallins: A Fluorescence Lifetime and Quenching Study," *Biochemistry*, 27: 810–820, 1988.

Auteri et al., "Laser Activation of Tissue Sealant in Hand-–Sewn Canine Esophageal Closure," *J. Thorac. Cardiovasc. Sur.*, 103: 781–783, 1992.

Bonneau et al., "pH Dependence of Singlet Oxygen Production in Aqueous Solutions Using Thiazine Dyes as Photosensitizers," *Photochemistry and Photobiology*, 21: 159–163, 1975.

Chacon et al., "Singlet Oxygen Yields and Radical Contributions in the Dye–Sensitized Photo–Oxidation in Methanol of Esters of Polyunsaturated Fatty Acids (Oleic, Linoleic, Linolenic and Arachidonic)," *Photochemistry and Photobiology*, 47(5): 647–656, 1988.

Chuck et al., "Dye–Enhanced Laser Tissue Welding," *Lasers in Surgery and Medicine*, 9: 471–477, 1989.

Ebert et al., "On the Introduction of Disulfide Crosslinks into Fibrous Proteins and Bovine Serum Albumin," pp. 235–245.

Fluhler et al., "Laser Intensity and Wavelength Dependence of Rose–Bengal–Photosensitized Inhibition of Red Blood Cell Acetylcholinesterase," *Biochimica et Biophysica Acta*, 990: 269–275, 1989.

Girotti et al., "Methylene Blue–Sensitized Photooxidation of Hemoglobin: Evidence for Cross–Link Formation," *Photochemistry and Photobiology*, 29: 1119–1125, 1979.

Goosey et al., "Cross–Linking of Lens Crystallins in a Photodynamic System: A Process Mediated by Singlet Oxygen," *Science*, 208: 1278–1280, 1980.

Goosey et al., "Effects of Singlet Oxygen on Human Lens Crystallins *in Vitro*," *Invest. Opthalmol. Vis. Sci.*, 20(5): 679–683, 1981.

Jernigan, Jr., Howard M., "Role of Hydrogen Peroxide in Riboflavin–Sensitized Photodynamic Damage to Cultured Rat Lenses," *Exp. Eye Res.*, 41: 121–129, 1985.

Lee and Rodgers, "Laser Flash Photokinetic Studies of Rose Bengal Sensitized Photodynamic Interactions of Nucleotides and DNA," *Photochemistry and Photobiology*, 45(1): 79–86, 1987.

Misra and Misra, "Vasoactive Intestinal Peptide, a Singlet Oxygen Quencher," *J. Biol. Chem.*, 265(26): 15371–15374, 1990.

Moazami et al., "Reinforcement of Colonic Anastomoses with a Laser and Dye–Enhanced Fibrinogen," *Arch. Surg.*, 125: 1452–1454, 1990.

Oz et al., "Tissue Soldering by Use of Indocyanine Green Dye–Enhanced Fibrinogen with the near Infrared Diode Laser," *J. Vas. Surg.*, 11: 718–725, 1990.

Oz et al., "In Vitro Comparison of Thulium–Holmium-–Chromium: YAG and Argon Ion Lasers for Welding of Biliary Tissue," *Lasers in Surgery and Medicine*, 9: 248–253, 1989.

Schober et al., "Laser–Induced Alteration of Collagen Substructure Allows Microsurgical Tissue Welding," *Science*, 232: 1421–1422, 1986.

Stimler and Tanzer, "Location of the Intermolecular Crosslinking Sites in Collagen," pp. 675–693.

Sinclair, Roy S., "Yearly Review. The Light Stability and Photodegradation of Dyes," *Photochemistry and Photobiology*, 31: 627–629, 1980.

Tanielian, Charles, "Photooxygénations Sensibilisées par les Colorants," *Biochimie*, 68: 797–806, 1986.

(List continued on next page.)

Primary Examiner—Susan W. Berman
Attorney, Agent, or Firm—Arnold, White & Durkee

[57] ABSTRACT

The present invention relates generally to the field of biological and medical adhesives and encompasses more specifically the closing of microsurgical wounds and other tissue wounds and defects due to surgical procedures or other causes. A medical adhesive comprising a photosensitizing species and an protein or peptide containing moiety are disclosed which may be applied to various tissues, an adhesive bond being formed by exposure of the adhesive to photoactivating radiation.

34 Claims, 1 Drawing Sheet

OTHER PUBLICATIONS

Tomlinson et al., "Photoinactivation of Acetylcholinesterase by Erythrosin B an Related Compounds," *Biochem. Cell Biol.*, 64: 515–522, 1986.

Watanabe et al., "Effect of Cysteine on Bovine Serum Albumin (BSA) Denaturation Induced by Solar Ultraviolet (UVA–UVB) Irradiation," *Chem. Pharm. Bull.*, 39(7): 1796–1801, 1991.

Wider et al., "Skin Closure with Dye–Enhanced Laser Welding and Fibrinogen," *Plastic Reconstr. Sup.*, 88(6): 1018–1025, 1991.

Yamasaki and Yano, "Differential Scanning Calorimetric Studies on Bovine Serum Albumin: II. Effects of Neutral Salts and Urea," *Int. J. Biol. Macromol.*, 13: 322–323, 1991.

Zyplast® Implant Physician Package Insert, Tagmet Product Brochure, Collagen Corporation, Palo Alto, CA 94303.

FIG. 1

ORGANIC TISSUE GLUE FOR CLOSURE OF WOUNDS

BACKGROUND OF THE INVENTION

1. Field of the Invention

The present invention relates generally to the field of medical and biological adhesives and encompasses more specifically the closing of microsurgical and large wounds in delicate tissues as well repair of tissue defects by medical and biological adhesives.

2. Description of the Related Art

The conventional methods of choice to close incisions in soft tissue following surgery, injury and the like have been sutures and staples in spite of the limitations which are inherent in these mechanical approaches. For example, tissue incompatibility with sutures or staples may cause fistulas granulomas and neuromas which are painful and difficult to treat. Sutures and staples may also tend to cut through weak parenchymatous or poorly vascularized tissue. Sutures also leave behind a tract which can allow for leakage of fluids and organisms. The needle for any suture is larger than the thread attached to it. This causes a problem as the needle tract is larger than can be filled by the thread.

In addition, limits are imposed by the required manual dexterity and eyesight of the surgeon and the excessive amount of time that is required for the use of sutures or staples in microsurgeries. Finally, even when properly applied, the joints in the gaps between the staples or sutures may be inherently weak or may structurally weaken over time and will leak.

Several investigators have worked on laser closure of wounds (White et al., 1986; White, J. V., 1989; Oz and Bass et al., 1989; White et al., 1987). Early contributions concentrated on welding tissues using lasers of different wavelengths applied directly to wound edges. Investigating the microstructural basis of the tissue fusion thus produced, Schober and coworkers proposed that there occurred a "homogenizing change in collagen with interdigitation of altered individual fibrils" (Schober et al., 1986). These investigators, as well as others, proposed that the concentrated heating of the collagen fibrils above a threshold level allowed for their cross-linking (Goosey et al., 1980; Chacon et al., 1988; Tanzer, M. L., 1973). Unfortunately, the heat necessary to allow this reaction to occur causes collateral thermal damage. Even a slight distortion, in ocular tissue for example, may have functional consequences. Also, in the event of laser weld failure, the edges of the tissues may be damaged by the original treatment and cannot be re-exposed to laser energy (Oz, 1990).

Further work attempted to enhance heat-activated cross-linking by placing a dye in the wound. It was reported that matching the absorbance of the dye with the laser wavelength, allowed an adhesive effect to be achieved with less laser power output and collateral thermal injury (Chuck et al., 1989; Foote, C. S., 1976; Oz M. C. and Chuck et al, 1989). Coupling the dye with a protein to create a tissue "solder" was also investigated. The protein of choice has been fibrinogen, and in particular autologous fibrinogen in order to avoid problems of the transfer of viral diseases through the use of blood components from pool donors. In previous applications, fibrinogen has been obtained as a fraction of whole blood. It is not pure fibrinogen, but also contains other blood elements, such as clotting factors. Application of such a protein-dye mixture in various animal models proved to be an improvement to dye alone (Oz et al., 1990; Moazami et al., 1990). Unfortunately, human application was forestalled owing to the need to isolate the needed protein (fibrinogen) from the patient prior to the procedure to avoid the risks of infection from donor plasma. Work with albumin found it to be an unsatisfactory substitute as it did not yield welds of comparable strength.

Comparisons of protein-dye versus sutured closures have found the protein-dye group to produce less of an inflammatory response, result in greater collagen production, greater mean peak stress at rupture and better cosmesis (Wider et al., 1991). Ophthalmologic application of such a tissue solder has included the sealing of conjunctival blebs (Weisz, et al., 1989), sclerostomy (Odrich et al., 1989), closure of retinectomies (Wolf et al., 1989), and thermokeratoplasty (Wapner et al., 1990) using similar mixtures.

Although several tissue adhesives have been formulated, few have seen widespread use clinically. "Laser-activated" tissue glues have been used in skin closures as well as vascular and bowel anastomoses (Chuck et al., 1989; Moazami et al., 1990; Wider et al., 1991; Auteri et al., 1992). The most successful product thus far is a mixture of cryoprecipitated fibrinogen and a dye that absorbs laser energy and releases it in the form of heat at the wound interface (Moazami, et al., 1990; Oz et al., 1990).

Because of the urgent need for a satisfactory method of closing wounds and surgical incisions in ocular tissue, the inventors tried systematically to find the best combination of protein and laser induced heat-generating dye for use in the eye. The results of this study led the inventors to conclude that all wounds closed in this manner are unsatisfactory. Adequate bond strengths in human cadaver sclera were only achieved at the cost of obvious protein denaturation and tissue distortion around the wound site. The process was arduous due to sclera's tendency to shrink when exposed to heat and the seal thus obtained diminished markedly in strength when immersed in water. This is especially important in vascular anastomoses or for any anastomoses of a fluid containing structure such as the eye, aorta, ureter and GI tract, in which the fluid contents may leak out. This is in addition to the problems mentioned above when fluids and bacteria may leak into a wound. In an environment such as the eye, overcoming this drawback was crucial to the success of the method of wound closure.

Although much work has been done in this area, there is still no method of closing wounds in tissues that does not have serious limitations. What is needed in the art is a method of producing a fast, water tight seal of a wound without the mechanical problems and manual dexterity associated with sutures and staples, and without the distortion and collateral tissue damage caused by heat-generating methods of wound closure.

SUMMARY OF THE INVENTION

The present invention overcomes these and other drawbacks in the prior art by providing improved compositions and methods for use in tissue closure and wound healing which are associated with reduced, or typically negligible, heat-production. The lack of heat allows an effective seal with minimal tissue distortion or damage to surrounding areas. The present invention also overcomes the difficulty, time and expense of preparing fibrinogen as a cryoprecipitated fraction of whole blood. In the present method, commercially available fibrinogen may be utilized which is much more pure, less expensive and less time consuming than the cryoprecipitated fractions that have been used in the past.

Heat production is evaluated by placing a small, sensitive temperature probe into the wound during application of the activating radiation. Tissue damage is evident upon visual inspection of the surrounding tissue. Negligible, minimal or no tissue damage is indicated by the absence of visible scarring or distortion of tissue and by the absence of any difference in tactile texture such as hardness associated with scarring. In order to determine whether tissue damage exists, cross-sections of tissue may be taken and stained with an appropriate histological stain and viewed under about 40× magnification. At this level of magnification, "no tissue damage" is indicated by a lack of charring or, for example, an amorphous coagulum within a region up to about 100 μm around the irradiated area, and a loss of nuclear detail and cellular integrity in an area up to 300 μm from the treated area. Carbon deposits or localized swelling are also not evident.

In certain embodiments, the present invention concerns novel compositions comprising a biocompatible protein or peptide containing composition in combination with a biocompatible photosensitizer. Although not intended exclusively for use in tissue sealing, the compositions of the invention may be referred to as a tissue or surgical adhesive, glue, or sealant, or a wound sealant. All of the foregoing terms are used herein to describe a combination of components capable of adhering, sealing, closing, apposing or otherwise joining, two or more soft tissue elements. A tissue glue thus preferably functions to promote, catalyze or otherwise generally cause the formation of covalent bonds between tissues, such as the edges of a wound or surgical incision, so that it promotes the formation of a proteinaceous framework between tissue elements allowing the formation or reconstruction of a biological seal.

As used herein, the term "biocompatible" refers to a substance which produces no significant untoward effects when applied to, or administered to, a given animal or human subject according to the methods and amounts described herein. Such untoward or undesirable effects are those such as significant toxicity or adverse immunological reactions. In preferred embodiments, biocompatible protein or peptide containing compositions will generally be mammalian proteins or peptides or synthetic proteins or peptides each essentially free from toxins, pathogens and harmful immunogens.

The compositions of the invention will generally comprise a biocompatible protein or peptide containing composition in combination with an amount of a biocompatible photosensitizer effective to promote the formation of an adhesive upon photoactivation. As used herein, the term "photoactivation" is used generally to describe the process by which energy in the form of electromagnetic radiation is absorbed by a compound which becomes "excited" and then functions to convert the energy to another form of energy, preferably chemical energy. The chemical energy will be in the form of reactive oxygen species like singlet oxygen, superoxide anion, hydroxyl radical, the excited state of the photosensitizer, photosensitizer free radical or substrate free radical species. The electromagnetic radiation will include "optical energy", i.e., will have a wavelength in the visible range or portion of the electromagnetic spectrum, and will also include the ultra violet and infra red regions of the spectrum. The photoactivation processes particularly associated with the present invention are those which involve reduced, negligible, or no conversion or transfer of the absorbed energy into heat energy and, hence, are associated with increased or enhanced transfer of the absorbed energy into chemical energy. The photoactivation occurs with no more than a 1–2 degree Celsius rise in temperature, preferably no more than 1° C. rise and more preferably no more than 0.5° C.

The term "photosensitizer", as used herein, refers to a compound capable of undergoing photoactivation as described above. Accordingly, photosensitizers can be characterized functionally as those chemicals which absorb electromagnetic energy, such as optical energy, and convert it primarily to chemical energy. Preferred photosensitizers for use in accordance herewith will be compounds capable of causing a photo-oxidative effect, and in particular, those capable of producing singlet oxygen when exposed to light.

In preferred embodiments, it is contemplated that one would wish to employ a substantially water-soluble photosensitizer, particularly where the photosensitizer, or combined composition, is intended for use in connection with a substantially aqueous tissue environment such as, e.g., the eye. However, water-solubility is only required to the extent that the photosensitizer is able to form a substantially soluble composition on contact with either the protein or peptide containing composition, the tissue itself, or a combination of the two. "Substantially soluble" indicates that the various components of the composition and tissue are able to functionally interact and that there is no significant particulate matter formed which may cause or contribute to an adverse biological reaction.

The photosensitizer element of the composition will be used in an amount effective to promote the formation of an adhesive upon photoactivation, i.e., to generate a photo-oxidative effect sufficient to form an adhesive. These terms are used to refer to the process by which the photosensitizer, when exposed to light, produces singlet oxygen in sufficient quantities to cause oxidative damage to amino acids. The damage, i.e., chemical modification, to the amino acids results in the formation of covalent bonds or cross-links between distinct amino acids, thus allowing the formation of a proteinaceous adhesive, seal or framework. It is the generation of this proteinaceous adhesive, using exogenous protein or peptide containing compositions and/or endogenous tissue components, which allows tissues to be sealed and wounds or other incisions to be closed.

This oxidative damage takes the form of the excited state of photosensitizer molecules and reactive oxygen species as well as substrate free radicals which are capable of reacting with a wide variety of compounds. The photosensitizers described herein may thus also be characterized as compounds capable of photo-oxidatively damaging or modifying the amino acids of the protein and thus causing the presence of highly reactive species and thus promoting the cross-linking reactions.

Examples of photosensitive compounds for use herewith include various light-sensitive dyes and biological molecules such as, for example, flavins, xanthenes, thiazines, porphyrins, expanded porphyrins, chlorophylis and any photosensitive derivatives thereof. As mentioned above, compounds which absorb and convert electromagnetic energy, but which release a substantial amount of heat energy and do not significantly produce reactive oxygen species, are not contemplated for use in the present invention. For example, fluorescein is a xanthene, but is not considered a photosensitizer as it releases absorbed energy primarily in the form of heat and fluorescence.

Preferred photosensitizers are contemplated to include xanthenes such as rose bengal and erythrosin; thiazines such as methylene blue; porphyrins and expanded porphyrins such as protoporphyrin I through protoporphyrin IX, coproporphyrins, uroporphyrins, mesoporphyrins, hematoporphyrins and sapphyrins; chlorophylis such as bacteriochlorophyll A and flavins such as riboflavin. Particularly preferred photosensitizer compositions will be those comprising riboflavin, and even more preferably, those comprising riboflavin-5-phosphate, or flavine mononucleotide, flavin adenine dinucleotide as well as flavin guanine nucleotide, flavin cytosine nucleotide and flavin thymine nucleotide compounds. These compounds will be utilized in the mono, di and tri phosphorylated species. The choice of photosensitizer will generally be made in conjunction with the choice of electromagnetic radiation contemplated for use in exciting the compound, as will be understood by those of skill in the art in light of the present disclosure.

It is contemplated that virtually any protein or peptide containing component may be used in the compositions and methods disclosed herein so long as it is biocompatible. In certain embodiments, it is envisioned that the formation of a more viscous composition will be advantageous in that will allow the composition to be more precisely or easily applied to the tissue and to be maintained in contact with the tissue throughout the procedure. In such cases, the use of a peptide composition, or more preferably, a protein composition, is contemplated.

Proteins and peptides suitable for use in this invention may be autologous proteins or peptides, although the invention is clearly not limited to the use of such autologous proteins. As used herein, the term "autologous protein or peptide" refers to a protein or peptide which is derived or obtained from a selected animal or human subject and used as a component of a composition intended for application to the selected animal or human subject. Autologous proteins or peptides are prepared, for example from whole plasma of the selected donor. The plasma is placed in tubes and placed in a freezer at about −80° C. for at least about 12 hours and then centrifuged at about 12,000×g for about 15 minutes to obtain the precipitate. The precipitate, such as fibrinogen may be stored for up to about one year (Oz, 1990).

In that the compositions of the present invention are particularly suitable for use in tissue adhesion and wound healing, preferred proteins are contemplated include proteins such as connective tissue proteins, plasma proteins and clotting cascade proteins. Particularly preferred proteins include, for example, collagen, keratin, elastin, albumin, myoglobin and fibrinogen, with fibrinogen being most preferred.

The novel compositions of the present invention may be formulated with any pharmacologically acceptable medium or diluent. Biocompatible formulations of protein or peptide containing compositions and photosensitizers may variously include aqueous solutions and physiological buffers and other agents, such as stabilizers and fatty acids. The protein content of the composition may be adjusted according to the viscosity of the composition desired, and in view of the intended use of the composition and the nature of any tissues to which it may be applied. In general, protein formulations of the correct viscosity are limited by the solubility of the protein. The solution is to be thick enough to stay in the wound and not so thick as to clot in the needle as it is being applied. The amount of photosensitizer needed is proportional to the protein concentration and will be determined for each application. The proportion of protein to photosensitizer is important, as too much photosensitizer will consume the oxygen radicals before they have a chance to cause a reaction and insufficient radicals will not generate enough reactive species to complete the reaction. The lifetime of the singlet oxygen will also vary with the concentration of the photosensitizer and of the solvent used. These variables can be determined for each application without undue experimentation by those of skill in the art.

In preparing a composition intended for application to a particular selected tissue, it is contemplated certain advantages may be gained by employing a protein or peptide known to be present within that selected tissue. One example of such a combination is the use of the crystallin lens protein in compositions intended for application to the eye.

The biocompatible proteinaceous and photosensitizing components of the novel compositions disclosed herein may be in the form of a single component system such that they form a single composition. Within the single composition, the components may be physically separate or they may be physically combined, for example, by the covalent attachment of a photosensitizer to a protein or peptide. This attachment may be achieved by any one of a variety of chemical coupling means known to those of skill in the art including, for example, the use of reducers, oxidants, acids, bases and other chemically reactive species such as $HCO_3$.

Alternatively, the compositions of the present invention may be in the form of dual or double component systems where both individual components are stored separately until use. In the latter case, a single composition may still be formed by mixing, or combining, the protein or peptide containing and photosensitizing components some time prior to use. Alternatively, each component may be applied separately to the tissue area or wound to be joined, such that the active composition will only be formed on irradiation of the tissue itself, i.e., it is only formed in situ. It will be understood that all such alternatives and combinations thereof fall within the scope of the present invention.

Further aspects of the invention concerns kits for use in forming an adhesive connection between biological tissues. Such kits will include a light-protected container comprising a biocompatible photosensitizer and a biocompatible protein or peptide containing composition as described above. It is particularly important that the photosensitive component be kept in the dark, i.e., in the light-protected container. Photosensitizers included in the kits in powdered form need to provided in water and water vapor tight containers and will be stored in refrigerated environments, for example from about 4° C. to as cold as about −80° C. However, as with the compositions, the kit may be in the form of a dual or double component kit system where the components are stored separately until use. In this case, there is no requirement that the protein or peptide containing component also be stored away from the light, and it may kept in a separate container of any form.

Suitable containers are contemplated to include light-protected tubes; plastic, dark glass or otherwise light-protected bottles, or light-tight foil wraps. Such containers may also comprise a means to apply the adhesive to the tissue, for example a collapsible tube, or a glass container with a plunger device to dispense the adhesive comprising a syringe like device. It is contemplated that such a device may comprise a syringe in which the protein and photosensitizer solutions are separated by a plate that contains serrations which will penetrate the photosensitizer containing compartment and then allow mixing of the contents of that compartment with the contents of the protein containing compartment (See FIG. 1). In that the operation of the kits will generally rely on photo-oxidative mechanisms and singlet oxygen generation, one may wish to store the photosensitizer and/or the protein or peptide containing compositions in a high oxygen atmosphere or in an atmosphere which has a higher oxygen concentration or tension than usual. As with any biological formulation, it is advisable to store these kits under refrigeration, such as at 4° C.

In still further embodiments, the present invention concerns methods for forming an adhesive connection between biological soft tissues or filling in damage to other tissues. To perform such a method or procedure, one would first prepare a composition as described herein and then apply the composition to the tissues to be connected to form a tissue adhesive combination. One would then irradiate the tissue adhesive combination, i.e., apply electromagnetic radiation to this area, in a manner effective to promote the formation of an adhesive connection between the tissues. The formation of an adhesive connection will be achieved by the photo-oxidative effects of singlet oxygen generating proteinaceous cross-links between the amino acid components of the composition and/or tissue.

The present invention also encompasses methods for tissue closing or wound healing wherein the actual preparation of a separate protein or peptide containing composition is not necessary. Such methods utilize the peptides or proteins located naturally within the tissue area as in situ protein containing compositions. To form an adhesive connection between biological tissues in this manner one would form a biologically effective amount of a tissue adhesive combination at the tissues by applying only the photosensitizer component to the tissues. One would then again apply electromagnetic radiation the tissue adhesive combination thus formed in a manner effective to promote the formation of an adhesive connection between the tissues.

In either of the methods described above, the amount of the composition used will, naturally, be dependent on the tissue(s) to which it is being applied and on the size and nature of the wound or incision to be closed or the distance between the tissues to be apposed. The determination of the appropriate amount of the composition to be applied will be known to those of skill in the art in light of the present disclosure. Likewise, the application of the electromagnetic radiation will also be adapted to suit the particular circumstances of operation. It is generally envisioned that the time for performing a tissue closure procedure in accordance herewith will be less than five minutes in total. For example, the closure of an incision of about 5 mm in length is contemplated to require in the order of 1 to 2 minutes.

A particular advantage of the present invention is the precision with which it can be used. Other glues that have been used stick wherever they are applied and much care must be taken to avoid the glue spilling over into areas where it is not desired. In the present invention, the glue is activated only where the practitioner applies the laser light and this can be a very small area, i.e. on the order of about 2 mm diameter. Thus any excess glue can be ignored or washed off. Thus the area of actual tissue adhesion is precisely controlled and is determined by the steadiness of the application of the laser energy. It is contemplated that even more precision is possible through the application of the laser energy by electronically controlled means.

The electromagnetic radiation necessary to achieve photoactivation will generally have a wavelength from about 10 nm to about 700 nm and will be within the visual, infra red or ultra violet spectra. The radiation will be supplied in the form of a monochromatic laser beam or other form of electromagnetic radiation source. The choice of energy source will generally be made in conjunction with the choice of photosensitizer employed in the composition. For example, an argon laser is particularly suitable for use with flavins such as riboflavin-5-phosphate, i.e., flavins are optimally excited at wavelengths corresponding to the wavelength of the radiation emitted by the argon laser. For similar reasons, a diode laser is particularly suitable for use with chlorophylis such as bacteriochlorophyll A, and an excimer laser is suitable for refractive surgeries. Suitable combinations of lasers and photosensitizers will be known to those of skill in the art, and are exemplified in Table 1.

TABLE 1

| Photosensitizer | Laser Source | Wavelength |
|---|---|---|
| Riboflavin-5-phosphate | Argon | 488–514 nm |
| Rose Bengal | Krypton Red | 600–670 nm |
| Porphyrins | Argon/Krypton/ | 488–514, |
|  | Tunable Dye Lasers | 546, 600–670 nm |

Tunable dye lasers are also used with the present invention. These lasers can be tuned to emit generally any wavelength within a broad spectrum and allow for exact matching of dye and laser wavelength. Application of this technology will be known to those of skill in the art.

The present invention is envisioned to be suitable for use in a variety of surgical embodiments where one desires to seal, close, appose or otherwise join two or more portions of soft tissue, or to fill in cavities or damage to soft or hard tissues. The invention is considered to be particularly suitable for use in microsurgery, such as, for example, in surgical operations or maneuvers concerning the eye, small vascular tissue, gastro intestinal tract, nerve sheaths, small ducts (urethra, ureter, bile ducts, thoracic duct) or even the inner ear. It is particularly suitable for procedures involving laparoscopic operations or interventions such as laparoscopic (LP) cholecystectomy, LP nephrectomy, LP thoracic procedures, LP appendectomy, LP hernia repairs, LP tubal ligations and LP orbital surgeries. The present invention will also be useful in retractive surgeries. However, these examples are clearly not limiting and the use of the methods and compositions described herein in connection with any type of wound closure or surgical procedure is encompassed by the invention.

In yet further embodiments, the present invention concerns methods for cross-linking proteins. Such methods comprise forming an effective amount of a protein cross-linker combination at the proteins to be cross-linked and irradiating the combination with electromagnetic radiation in a manner effective to promote the formation of cross-links between the proteins. The protein cross-linker combination may be formed by preparing a composition in accordance herewith and applying the composition to the proteins to be cross-linked, or by applying only the photosensitizer component itself to the proteins. The choice of electromagnetic radiation and photosensitizer will be coordinated as discussed above and as exemplified by the combinations listed in Table 1.

Cross-linking proteins in this manner is contemplated to be of use in a variety of non-clinical embodiments such as, for example, in cross-linking proteins for use in chromatographic columns or beads, the immobilization of antibodies or antigens for diagnostic or purification purposes, or for the fixing of proteins for microscopy.

BRIEF DESCRIPTION OF THE DRAWINGS

Mixing is achieved on moving the plunger of the mixing syringe back and forth. A syringe such as shown in the figure could be stored under high oxygen tension and the entire containing system protected from the light, for example, by covering with lightproof foil. The numbers in the figure represent the following functional parts: (1) Protein; (2) Plunger with holes used to break the dye out of its container and to mix the solution; (3) Serrations on back of plunger; (4) Dye container; (5) Membrane which is torn by the serrations and allows the dye to be mixed through the holes; and (6) Plunger to push the contents out. A needle or nozzle may be optionally attached to the syringe for application of the combined adhesive composition to tissues or proteins.

DETAILED DESCRIPTION OF THE PREFERRED EMBODIMENTS

There has been much interest recently in the development of tissue adhesives. Several have been formulated although few have seen widespread use clinically. The hitherto most successful product is a mixture of cryoprecipitated fibrinogen and a dye that absorbs laser energy and releases it in the form of heat at the wound interface (Moazami, et al., 1990; Oz et al., 1990).

Both thermal and photodynamic pathways for closing corneal wounds without sutures were investigated by the present inventors. However, the project was begun with only the idea of systematically finding the best combination of protein and heat-generating dye possible for use in the eye. For the protein moiety, bovine serum albumin, Zyplast collagen, acid-soluble collagen, myoglobin, and fibrinogen were tested. It is contemplated that cryoprecipitated fibrinogen from fresh plasma was a possible protein moiety, however it was not chosen due to the inconsistency of the concentration of desired components and the presence of impurities that remain in such extracts. In addition, obtaining cryoprecipitated fibrinogen is a costly and time consuming process.

The present invention, by utilizing pure, commercially available protein or peptide containing preparations, overcomes the problems associated with cryoprecipitated fibrinogen as well as the risk of transmission of viral infections inherent in the use of pooled donor blood. The present invention also overcomes the problem of the time involved in obtaining autologous proteins which in some cases, for instance in emergency situations, is impossible.

The proteins were used in conjunction with the following dye-laser combinations: fluorescein-argon, Fluorescein isothiocyanate-argon, FD&C Red #40-argon, FD&C Yellow #6-argon. Attempts were also made to increase bond strength by using reduced glutathione, ethanol, and hyaluronic acid, but these additives were ineffective. Adequate bond strengths in human cadaver sclera were only achieved at the cost of obvious protein denaturation and tissue distortion around the wound site. The process was arduous due to sclera's tendency to shrink when exposed to heat and the seal thus obtained diminished markedly in strength when immersed in water.

After testing of the adhesives containing heat producing dyes, the inventors investigated a new class of substances called photosensitizers. These chemicals cause photo-oxidative effects when exposed to visible light (Chacon et al., 1988; Tanielian C., 1986; Foote, C. S., 1976). There are four major classes of photosensitizers: flavins (riboflavin), xanthenes (erythrosin, rose bengal), thiazines (methylene blue), and porphyrins (protoporphyrin IX, uroporphyrin, hematoporphyrin derivatives). Fluorescein is a xanthene but is not considered a photosensitizer because it releases absorbed energy primarily in the form of heat and fluorescence.

The effect of photosensitizers in the present invention is surprising due to their typical use as cytotoxic or histotoxic agents in the presence of light. The highly reactive free radical and radical anion species produced by these agents have been shown to cause oxidative damage to human lens enzymes (Jedziniak, 1987) and to ocular proteins of other species. This histotoxic effect has also been exploited in their use in photodynamic cancer therapies.

There are two major types of sensitized photo-oxidative process, Type I and Type II. The sensitizer in its ground state $S_0$ first absorbs light energy to form $S_1$ and $T_1$ which are sensitizer molecules in their excited singlet and triplet states, respectively. Both Type I and Type II reactions then proceed via the triplet state because it has a much longer lifetime than the singlet state.

In Type I reactions, the sensitizer triplet $T_1$ then directly binds to the substrate to produce substrate free radicals or radical anions. The substrate radicals then can undergo further reactions, including that with molecular oxygen to form the superoxide anion $O_2^-$. The superoxide anion then can react in numerous ways. For example, the superoxide anion can further react to generate hydrogen peroxide ($H_2O_2$) and the hydroxyl radical (OH.).

In Type II reactions, the sensitizer triplet most commonly reacts first with molecular oxygen to produce singlet oxygen ($^1O_2$) The singlet oxygen then oxidizes the substrate to form photo-oxidation products. Direct electron transfer from triplet to oxygen also occurs to yield superoxide anions but much less efficiently.

Photosensitizers then cause oxidative damage to susceptible amino acid residues, namely histidine, tryptophan, tyrosine, cysteine, and methionine. They are known to cause non-disulfide covalent cross-links in susceptible proteins (Goosey et al., 1980; Girotti et al., 1979). This process is oxygen dependent and seems to be mediated by singlet oxygen rather than by superoxide anions, hydrogen peroxide, or hydroxyl radicals. Natural collagen is devoid of disulfide bridges (Stimler et al., 1977). The present invention enables one to address the question whether photosensitizers can produce non-disulfide covalent cross-links within collagen when exposed to light.

In the present invention, water soluble photosensitizers that have high quantum efficiency for singlet oxygen production were selected. These photosensitizers included rose bengal (excited by the argon laser), riboflavin-5-phosphate (argon laser), porphyrins (argon/krypton) and methylene blue (krypton laser). The photosensitizer was then mixed with a protein solder, applied to the wound, and exposed to the appropriate laser. An 18% fibrinogen solution had the right consistency for ease of application and dissolved all photosensitizers without problem. Welded fibrinogen has been shown to resorb in vivo (Oz and chuck et al., 1989) and is thus a good substrate for an organic glue. Other proteins included in the present invention include albumin, zyplast collagen, myoglobin, glutathione, acid soluble collagen, $\beta_H$ crystallin, $\beta_L$ crystallin and lysine, at various concentrations and in combinations with each other and with various photosensitizers and salts. For a complete list of formulations, see Table 2.

TABLE 2

PROTEIN/PHOTOSENSITIZER MIXTURES

Saline + Fluorescein isothiocyanate
Saline + Fluorescein isothiocyanate + HCO3
25% Albumin + Fluorescein isothiocyanate
25% Albumin + Fluorescein isothiocyanate (1:1) + HA (1:1)
25% Albumin + Fluorescein isothiocyanate (1:1) + HCO3**
25% Albumin + Fluorescein isothiocyanate (1:1) +
HCO3 + HA (1:1)
25% Albumin + Fluorescein isothiocyanate (10:1) + HCO3
25% Albumin + Fluorescein isothiocyanate (10:1) +
HCO3 + HA
25% Albumin + Fluorescein isothiocyanate (1:1) +
HCO3 + 20% ETOH
25% Albumin + Fluorescein isothiocyanate (1:1) +
HCO3 + 50% ETOH
25% Albumin + Fluorescein
25% Albumin + Fluorescein + HA
Zyplast (collagen) + 10% Fluorescein
Zyplast + Saline + HCO3 + Fluorescein
isothiocyanate
Zyplast + Saline + HCO3 + Fluorescein
isothiocyanate + HA
35% Albumin + Fluorescein
35% Albumin + Fluorescein + HA
35% Albumin + Fluorescein isothiocyanate (1:1) +
HCO3 + 20% ETOH
35% Albumin + Fluorescein isothiocyanate (1:1) +
HCO3 + 10% ETOH
35% Albumin + Red # 40**
35% Albumin + Yellow #6
50% Albumin (fatty acid, globulin free) +
Fluorescein isothiocyanate (1:1) + Saline + HCO3
50% Albumin + Fluorescein isothiocyanate (1:1) +
HCO3 + 10% ETOH
50% Albumin + 10% ETOH
44% Myoglobin + Saline
44% Myoglobin + Saline + HA
10% Myoglobin + Saline
10% Myoglobin + Saline + HA
1% Myoglobin + Saline
1% Myoglobin + Saline + HA
5 uM Myoglobin (1:1 with Albumin) + 25% Albumin
10 uM Myoglobin (2:1 with Albumin) + 25% Albumin
5 mM Glutathione + Saline + Fluorescein
isothiocyanate + HCO3 + HA
50 mM Glutathione + Saline + Fluorescein
isothiocyanate + HCO3 + HA
5 mM Glutathione (1:1) + 35% Albumin +
Fluorescein isothiocyanate + HCO3
5 mM Glutathione + 35% Albumin + Fluorescein
isothiocyanate + HCO3 + HA
55 mg Glutathione (70:1) + 35% Albumin +
Fluorescein isothiocyanate + HCO3
50 mM Glutathione + 35% Albumin + Fluorescein
isothiocyanate + HCO3
50 mM Glutathione + 35% Albumin + Fluorescein
isothiocyanate + HCO3 + HA
HA + Saline + Fluorescein isothiocyanate + HCO3
Rose Bengal (2 mM) + 35% Albumin
Rose Bengal (0.2 mM) + 35% Albumin
Rose Bengal (0.02 mM) + 35% Albumin
Rose Bengal (20 uM) + 35% Albumin**
Rose Bengal (2 uM) + 35% Albumin
Rose Bengal (8 mM)
Rose Bengal (1 mM)
Methylene Blue (500 uM) + 35% Albumin + Argon Laser
Methylene Blue (500 uM) + 35% Albumin + Krypton Laser
Methylene Blue (50 uM) + 35% Albumin + Krypton Laser
Methylene Blue (5 uM) + 35% Albumin + Krypton Laser
2% Collagen (from Calf Tendon, dissolved in
acetic acid) + Rose Bengal (1:1) (Ph adjusted to
9 with NaOH)
3.8% Fibrinogen + De-ionized H2O + Rose Bengal
(Ph adjusted)
BH Crystallin + De I H2O + RB + NaOH
BL Crystallin + De I H2O + RB + NaOH
Collagen (1.7%) + Riboflavin-5-Phosphate (R5P)
(Ph adjusted)

TABLE 2-continued

PROTEIN/PHOTOSENSITIZER MIXTURES

Collagen (1.7%) + (R5P) (Ph adjusted) +
Glutathione (70:1)
3.8% Fibrinogen + R5P
3.8% Fibrinogen + R5P + Glutathione (70:1)
18% Fibrinogen + R5P (1:1)
18% Fibrinogen + R5P (10:1)**
18% Fibrinogen + R5P (10:1) + Na Azide
18% Fibrinogen + Fluorescein isothiocyanate +
HCO3**
18% Fibrinogen + Fluorescein isothiocyanate +
HCO3 + R5P (10:1)
Lysine + 18% Fibrinogen + R5P (10:1)
Lysine + De I H2O + R5P (10:1)

The best results were obtained with the combination of riboflavin-5-phosphate and fibrinogen in conjunction with the argon laser. This mixture was simple to manufacture and use, offered a water-tight seal, good bond strength and water stability, and no measurable heat production. The inventors were able to measure a temperature rise within the wound with fluorescein isothiocyanate but none within 0.1° C. with riboflavin-5-phosphate. Also, there was no obvious tissue distortion at the completion of the bond with the riboflavin-5-phosphate formulation. This last quality is of paramount importance in the eye, where, in particular, any distortion would inevitably result in functional, i.e. optical, degradation.

To measure the contribution of Type II reactions (mediated by singlet oxygen), the singlet oxygen quencher, sodium azide was added to the mixture of fibrinogen and riboflavin-5-phosphate. The resulting bond strength was significantly reduced but far from nonexistent, indicating a role for Type I reactions as well.

The present invention comprises a new organic tissue glue which can reliably close microsurgical incisions and other tissue wounds or defects without heat generation or surrounding tissue distortion. Animal experiments are to be conducted to determine the optimal formulations for in vivo application. Wound strength and the effects of the present method of wound healing on the shape of the cornea during the process of wound healing are also to be determined. The possibility of toxic reactions in the rest of the eye or other tissue being treated will be eliminated before human trials begin.

The primary use of this invention is in surgical applications where precise adhesion is necessary and where the application of sutures or staples is inconvenient or less effective than tissue adhesive. The adhesive of the present invention has uses in closing large wounds and tissue defects as in filling in a defect caused by debridement. Another use is as an artificial skin or covering agent to cover large, oozing surfaces inside or outside the body. Other uses include the repair of large, internal areas which are raw, or friable and which leak fluid and blood; reinforcement for a sutured anastomosis, thus rendering it water tight and bacteria tight; apposing parts of the body which are normally held together by surface tension such as the lung and chest wall; and to seal leaking blebs in the lung which are very difficult to treat.

The following examples are included to demonstrate preferred embodiments of the invention. It should be appreciated by those of skill in the art that the techniques disclosed in the examples which follow represent techniques discovered by the inventor to function well in the practice of the invention, and thus can be considered to constitute preferred modes for its practice. However, those of skill in the art should, in light of the present disclosure, appreciate that many changes can be made in the specific embodiments which are disclosed and still obtain a like or similar result without departing from the spirit and scope of the invention.

EXAMPLE I

Determination of the Strength of Various Adhesive Formulations

A. Materials and Methods

Fibrinogen, 35% albumin solution, fluorescein isothiocyanate (FITC), fluorescein, sodium azide, and riboflavin-5-phosphate (R5P) were obtained from Sigma Chemical. The 8.4% sodium bicarbonate is that normally used for intravenous infusions. Frozen non-preserved human cadaver eyes were from the Illinois Eye Bank.

All glue mixtures were made within two hours of use. The glue container was then wrapped in aluminum foil until ready for use. The eyes were defrosted in room temperature water. An 18 gauge butterfly needle was connected with a water bottle. The bottle's inner pressure was controlled by a hand-pumped sphygmomanometer. The needle was inserted in the vitreous cavity through equatorial sclera and the eye was pressurized to 25–30 mm Hg. The corneal epithelium was then removed at the wound site. A caliper set on 5 mm was used to mark the extent of the incision across central cornea. A simple through-and-through incision was made with a disposable sharp blade. The anterior chamber was then reformed with air. The glue was applied in a thin layer to the surface of the wound with a TB syringe and a 30 gauge needle. A small amount was then injected within the wound throughout its extent.

Argon laser (488–514 nm, HGM Argon) at a setting of 0.6 watts, 2 mm spot size was applied to the wound for 2 minutes in a continuous back and forth manner using the hand-held fiber optic probe. The laser was then directed at the remaining glue on the corneal surface until loss of fluorescence of the dye which took another 30–45 seconds. The sphygmomanometer was then pressurized in approximately 10 mm Hg increments. Bursting pressure was recorded the moment the wound leaked air or intraocular fluid. Temperature differences were measured to 0.1° C. sensitivity.

1. Experiment 1A. The first formulation contained 2.6 mg of R5P dissolved in 1cc of 18% fibrinogen in de-ionized water. Ten eyes were used in this experiment.

2. Experiment 1B. The second formulation was identical to the first, except that 0.03M sodium azide was added. Ten eyes were used in this experiment.

3. Experiment 2. The formulation was identical to Experiment 1A (i.e. no sodium azide was added.) Lasered eyes and the imbedded 18 gauge cannula were immersed in water at room temperature. The immersion times were recorded and the eyes were then burst in air as usual. The mean immersion time was 40 minutes. Ten eyes were used in this experiment.

4. Experiment 3. The formulation contained 1 cc of 18% fibrinogen, 1 mg Fluorescein isothiocyanate, and 0.1 cc 8.4% sodium bicarbonate. Three eyes were used in this experiment.

5. Experiment 4. The formulation was identical to that in Experiment 3 except that 35% albumin was substituted for the fibrinogen. Four eyes were used in this experiment.

6. Experiment 57 A small sensitive probe was placed within the wound to measure the maximal temperature reached during wound closure. Temperature values obtained with fibrinogen-Fluorescein isothiocyanate formulations were compared temperature values obtained with fibrinogen-R5P formulations.

B. Results

The bursting pressures obtained for the formulations of experiments 1–4 along with the standard deviations are presented in Table 3.

The exposure times and power densities were obtained empirically using human sclera during previous experimentation. The R-5P dye blanched well before the two minute exposure time was over. The fibrinogen mixture consistency was such that it was applied easily and maintained its position in the wound.

The Fluorescein isothiocyanate did not bleach with laser application. The albumin mixture was comparatively hard to handle as it tended to run off. Addition of hyaluronic acid (HA) did increase the viscosity of the mixtures but tended to weaken bond strength (results of separate experiments not reported).

Statistical analysis of the decrease in bond strength from the fibrinogen/R5P mixture with the addition of sodium azide was statistically significant (A<0.005). Comparison of the fibrinogen/R5P with the fibrinogen/Fluorescein isothiocyanate mixtures found the R5P to be statistically stronger (A<0.01). Comparison of fibrinogen/R5P with albumin/Fluorescein isothiocyanate mixtures found the stronger R5P bonds to be statistically significant (A<0.005).

TABLE 3

| Experiment # | Mean Bursting Pressure | Standard Deviation |
| --- | --- | --- |
| 1A | 154 mm Hg | 55 mm Hg |
| 1B | 80 mm Hg | 41 mm Hg |
| 2 | 219 mm Hg | 55 mm Hg |
| 3 | 60 mm Hg | 21 mm Hg |
| 4 | 37 mm Hg | 15 mm Hg |

EXAMPLE II

Formulation of Tissue Adhesive

A. Single component formulation

The protein moiety is mixed at the proper concentration with the photosensitizer in a sterile aqueous solution. Alternatively, the protein may be chemically coupled or attached to the photosensitizer. The attachment may be a covalent or a non-covalent attachment or bonding. The solvent is chosen as the appropriate solvent for the particular protein and photosensitizer and may be, but is not limited to deionized water, saline or ethanol of about 10% to about 50% and which may contain $HCO_3$, hyaluronic acid (HA), sodium hydroxide, glutathione, calcium or other suitable compounds. Any biocompatible agent which one desires may be added to adjust the viscosity and the pH of the solution and to improve bond strength. Other compounds such as vitamins, antibiotics or other compounds which have a secondary effect at the site of the application may also be added to the formulation.

The protein or peptide component is present at a concentration of on the order of about 1% to on the order of about 50% of the total solution and may contain one or more biocompatible proteins or peptides. The inventors found 18% fibrinogen to be of use in a corneal application. The concentration of the protein will in part be determined by the solubility of the protein and the viscosity obtained. The important factor in photosensitizer concentration is the proportion of photosensitizer to protein. It is important that the proportion is neither too high nor too low in order for the adhesive to be effective. The pH of the solution is in the range of about pH 6 to about pH 9.

B. Two-Component Formulation

Figure 1:
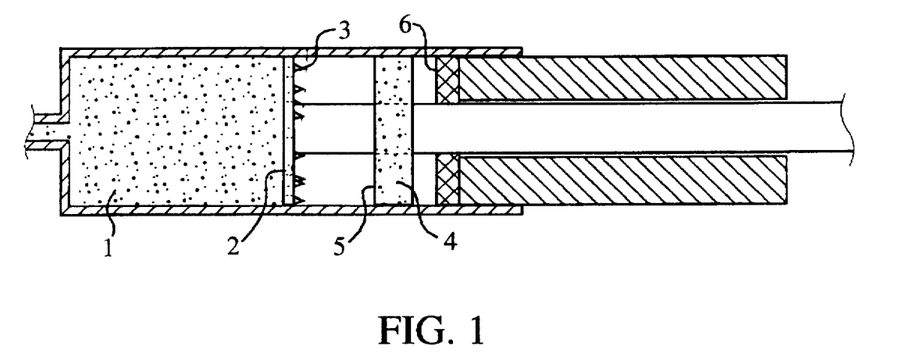
FIG. 1. Syringe for use in containing, and then mixing, the biocompatible protein or peptide compositions and the biocompatible photosensitizer compositions of the invention.

The formulation of Example IIA can also be formulated as a two component system in which the protein moiety is packaged separately from the photosensitizer and the two components may be mixed either just prior to application or mixed in situ. A possible method of mixing the two components is illustrated in FIG. 1. In the device of this figure, the two components are contained in compartments in a syringe like device and are mixed in the device just prior to application.

In an alternate embodiment of this example, the protein moiety may be the intrinsic proteins or peptides that are present in the tissue itself and the photosensitizer solution may be comprised of those elements of the above described one component system, with the exception of the protein or peptide component.

EXAMPLE III

Methods of Administering Adhesive

The formulations in the previous two examples may be applied to the wounded tissue through a needle, or dripped onto the wound from a dropper or in any manner suitable to the particular tissue. Alternatively, the adhesive may be placed onto a solid matrix which is then placed on the wound before activation. In an embodiment of the two component system, the two components may be contained in a applicator device which holds them in separate compartments and mixes the two components together as they are applied (See FIG. 1). The adhesive is then exposed to electromagnetic radiation or light for an appropriate time for the cross-linking reaction to occur in the particular tissue. Of course the adhesive and method of the present invention are applicable to tissues that are in situ, or located in the animal or human subject and are also applicable to ex vivo tissues, or tissues or organs that have been removed or exist outside an animal or human subject. The irradiation can be applied by a hand held or stationary instrument or through a fiber optic device or by any other method that is understood by those of skill in the art.

EXAMPLE IV

Kit Containing Tissue Adhesive

Further aspects of the invention concern kits for use in forming an adhesive connection between specific types of biological tissues. Such kits will include a light-protected container comprising a biocompatible photosensitizer and a biocompatible protein or peptide containing composition as described above. It is particularly important that the photosensitive component be kept in the dark, i.e., in the light-protected container, for example a tube, vial, bottle, syringe, or foil wrap which may be water tight and water vapor tight. However, as with the compositions, the kit may be in the form of a dual or double component kit system where the components are stored separately until use. In this case, there is no requirement that the protein or peptide containing component also be stored away from the light, and it may kept in a separate container of any form. The kit may also contain components such as the protein or photosensitizer or other components in powdered or lyophilized form to be stored in a freezer at about −20° C. to about −80° C. and to be mixed with solvents in the indicated concentrations just prior to use. All of the said solvents may or may not be provided with the kit.

The kit may also comprise a means to apply the adhesive to the tissue, for example a collapsible tube, or a glass or plastic container or a container of any other suitable material with a reservoir or connection to a reservoir and a plunger or other device to dispense the adhesive. In that the operation of the kits will generally rely on photo-oxidative mechanisms and singlet oxygen generation, one may wish to store the photosensitizer and/or the protein or peptide containing compositions in a high oxygen atmosphere or in an atmosphere which has a higher oxygen concentration or tension than usual. As with any biological formulation, it is advisable to store these kits under refrigeration, such as at 4° C. or as mentioned above.

EXAMPLE V

Non-Optical Clinical Uses

In addition to uses in microsurgical procedures, this invention is envisioned to be of use in surgery connected with large wounds and tissue defects. This use is exemplified not by closing two edges of a wound or incision, but rather by tissue "filling" in connection with correcting pre-existing defects or those caused by surgical intervention. For instance, after removing a cancer from a patient with bone cancer, the defect in the bone must be repaired or it will be filled with blood or other body fluids. It is known that any fluid filled cavity in the body is a great source for infection and so this should be avoided. Such defects can therefore be advantageously filled with the tissue glue of the present invention before the rest of the wound is closed over.

The present invention can also be used in delicate tissues and less, or not so delicate tissues. One such use is as an "artificial skin" or covering agent to cover large, oozing surfaces inside or outside the body. Burn patients, for example, could be covered with this material to assist in preventing bacterial infection and to lessen their loss of body fluids and electrolytes through their burned areas. The covering agent concept can also have other applications. Internally, surgeons often find large areas which are "raw" or "friable" and which leak fluid and blood. The glues of the invention are contemplated for use in such instances when they could be applied over such areas to prevent further leakage.

The biological adhesives described herein can also be used to reinforce sutured anastomosis. Sutures leave a tract behind which can allow for leakage of fluids and organisms. This is because the needle for any suture is larger than the thread attached to it and, therefore, the needle tract is larger than can be filled by the thread. The problem of leakage is especially important in vascular anastomoses or for any anastomoses of a fluid-containing structure (aorta, ureter, GI tract, eye, etc.) where the fluid or contents inside can leak out through the suture hole. It is envisioned that a wound could be sutured according to general procedures and then covered with a glue of the present invention, thereby making it water tight, impermeable to bacteria, and leaving no chance for leakage either into or out of the wound.

The present glues can also be used to oppose parts of the body which are normally held together by surface tension—like the lung and chest wall. When air is introduced into the space between the lung and the inner chest wall, the lung collapses as the surface tension holding the two structures together is lost. The glue can hold the lung back to the wall and also create an air tight seal that will prevent further collapse. The glue can also be used to seal "leaking blebs" in the lung itself—which are known to often be very difficult to treat.

EXAMPLE VI

Use in Refractive Surgery

The present invention is also considered to be particularly suitable for use in refractive surgery. "Refractive surgery" refers to the correction of irregularities or defects in the cornea. These procedures utilize an excimer laser which functions to remove or "shave" an even layer off the cornea. However, if the cornea contains irregularities, such as valleys, then this process only serves to preserve such irregularities in the newly-formed layer. The advantage of using the glue of the present invention would be that such valleys could be filled to create a smooth surface prior to the application of the laser, such that laser application would then create a new smooth layer. The inventors contemplate that the precise composition of the glue could be straightforwardly adapted to conform to the hardness of the cornea.

Another related use of this invention is in connection with re-shaping the cornea to achieve a different curvature. The glues may be employed to create a new structure which is matched to the curvature of a particular contact lens. The contact lens could be removed at a later stage and an excimer laser employed to complete the re-designing process and to smooth the finished surface.

EXAMPLE VII

Antiseptic Bandage

The present invention also comprises the embodiment of a bandage for nonsurgical, household use in which a strip of protein fiber or fiber of another biocompatible material is impregnated with the adhesive of the present invention and may be applied to a wound and photoactivated with a visible light source such as an incandescent, fluorescent or mercury vapor light source, including xenon arc lamps, or a laser light source.

The photoactivated bandage of this embodiment may contain other beneficial materials which include, but are not limited to, antibiotics, calcium, or any other biocompatable agent or composition that is desired to alter the viscosity or other physical characteristics of the solution.

The bandage strips will be individually stored in light protected containers or packages and, as necessary stored in refrigeration, for example at about 4° C. until used. When needed the bandage of the present invention will be placed on the wound and irradiated with the appropriate light source, thus forming an antiseptic barrier for the wound that does not need to be removed or replaced.

EXAMPLE VIII

A Method of Cross-linking Proteins without Heat Generation

The present invention also comprises a method of cross-linking proteins or other amino acid containing entities to other proteins or amino acids, to themselves and to other non protein materials without exposing the materials to damaging heat or ultra violet radiation. It is contemplated that this embodiment of the present invention would have utility in linking proteins or peptides or other amino acid species to solid matrices or to beads for use in chromatographic or immunological applications. Another use of this aspect of the invention is in the fixing of proteins for microscopy.

While the compositions and methods of this invention have been described in terms of preferred embodiments, it will be apparent to those of skill in the art that variations may be applied to the composition, methods and in the steps or in the sequence of steps of the method described herein without departing from the concept, spirit and scope of the invention. More specifically, it will be apparent that certain agents which are both chemically and physiologically related may be substituted for the agents described herein while the same or similar results would be achieved. All such similar substitutes and modifications apparent to those skilled in the art are deemed to be within the spirit, scope and concept of the invention as defined by the appended claims.

REFERENCES

The following references, to the extent that they provide exemplary procedural or other details supplementary to those set forth herein, are specifically incorporated herein by reference.

Auteri JS, Oz MC, Jeevanandam VJ, Sanchez JA, Treat MR, Smith CR. Laser Activation of Tissue Sealant in Hand-Sewn Canine Esophageal Closure. J Thor Card Surg 1992; 103:781–783.

Chacon JN, McLeary J, Sinclair RS. Singlet Oxygen Yields and Radical Contributions in the Dye-sensitised Photo-oxidation in Methanol of Esters of Polyunsaturated Fatty Acids (Oleic, Linoleic, Linoleic and Arachidonic). Photochem Photobiol 1988; 47:647–656.

Chuck RS, Oz MC, Delohery TM, Johnson JP, Bass LS, Nowygrod R, Treat MR. Dye-enhanced Laser Tissue Welding. Lasers Surg Med 1989; 9:471–477.

Foote CS. In Free Radicals in Biology. WA Pryor, Ed. Vol 2, p 85, Academic Press, New York, 1976.

Girotti AW, Lyman S, Deziel MR. Methylene Blue-Sensitized Photooxidation of Hemoglobin: Evidence for Cross-link Formation. Photochem Photobiol 1979; 29:1119–1125.

Goosey JD, Zigler JS, Kinoshita JH. Crosslinking of Lens Crystallins in a Photodynamic System: a Process Mediated by Singlet Oxygen. Science 1980; 208:1278–1280.

Jedziniak J, Arredondo M, Andley U. Oxidative Damage to Human Lens Enzymes. Current Eye Research 1987; 6:345–350.

Moazami N, Oz MC, Bass LS, Treat MR. Reinforcement of Colonic Anastomoses with a Laser and Dye-Enhanced Fibrinogen. Arch Surg 1990; 125:1452–1454.

Odrich SA, Eaton AM, Schubert H. Fluorescein Dye-enhanced Laser Sclerostomy. Abstract presented at ARVO 1989:934.

Oz MC, Bass LS, Popp HW, Chuck RS, Johnson JP, Trokel SL, Treat MR. In Vitro Comparison of THC:YAG and Argon Ion Lasers for Welding of Biliary Tissue. Lasers Surg Med 9:248–253 (1989).

Oz MC, Chuck RS, Johnson JP, et al. Indocyanine Green Dye-enhanced Welding with a Diode Laser. Surg Forum 1989; 40:316–8.

Oz MC, Johnson JP, Prengi S, Chuck RS et al. Tissue Soldering by Use of Indocyanine Green Dye-enhanced Fibrinogen with the Near Infrared Diode Laser. J Vasc Surg. 1990; 11:718 –25.

Schober R, Ulrich F, Sander T, Durselen H, Hessel S. Laser Induced Alteration of Collagen Substructure Allows Microsurgical Tissue Welding. Science 232:1421–2, 1986.

Stimler NP, Tanzer ML. Location of the Intermolecular Crosslinking Sites in Collagen. In Protein Crosslinking-Biomedical and Molecular Aspects, ed Friedman M. Advances in Experimental Medicine and Biology 1977; 86A:675–693.

Tanielian C. Photooxygenations Sensibilisees par les Colorants. Biochimie 1986; 68:797–806.

Tanzer ML. Cross-linking of Collagen. Science 1973; 180:561–6.

Wapner FJ, Eaton AM, Trokel SL, Schubert HD, Chuck RS, Treat M. Dye Enhanced Laser Thermokeratoplasty. Abstract presented at ARVO 1990:1600–3.

Weisz JM, Eaton AM, Libutti SK, et al. Repair of Conjunctival Filtering Bleb Using a Laser Activated Tissue Adhesive. Abstract presented at ARVO 1989; 381–87.

White JV. Laser Tissue Repair with the CO2 Laser. Poc SPIE 1989; 1086.

White RA, Kopchok G, Donayre C. Argon Laser Welded Arteriovenous Anastomoses. J Vasc Surg 1987; 6:447–453.

White RA, Kopchok G, Donayre C, Abergel RP, Lyons R, Klein SR, Dwyer RM, Uitto J. Comparison of Laser Welded and Sutured Aortotomies. Arch Surg, 1986; 121:1133–1135.

Wider TM, Libutti SK, Greenwald DP, Oz MC, Yager JS, Treat MR, Hugo NE. Skin Closure with Dye-Enhanced Laser Welding and Fibrinogen. Plastic Reconstr Surg 1991; 88:1018–1025.

Wolf MD, Arrindell EL, Han DP. Retinectomies Treated by Diode Laser Activated Indocyanine Green Dye Enhanced Fibrinogen Glue. Abstract presented At ARVO 1989; 3121–47.

What is claimed is:

1. A composition comprising from about 1% (w/v) to about 50% (w/v) of a biocompatible peptide in solution and in combination with an amount of a flavin photosensitizer capable of producing reactive oxygen species and effective to promote the formation of an adhesive upon photoactivation without more than about 2° C. rise in temperature.

2. The composition of claim 1, wherein the photosensitizer is riboflavin-5-phosphate.

3. The composition of claim 1, wherein the photosensitizer is attached to the peptide.

4. The composition of claim 1, further defined as comprising a biocompatible protein.

5. The composition of claim 4, further defined as comprising an autologous protein.

6. The composition of claim 4, further defined as comprising a connective tissue protein, a plasma protein or a clotting cascade protein.

7. The composition of claim 6, further defined as comprising one or more of collagen, keratin, elastin, hyaluronic acid, albumin, myoglobin or fibrinogen.

8. The composition of claim 4, further defined as comprising crystallin lens protein.

9. The composition of claim 4, further defined as comprising fibrinogen.

10. The composition of claim 9, wherein the fibrinogen is autologous fibrinogen.

11. The composition of claim 9, wherein the fibrinogen is an 18% fibrinogen formulation.

12. The composition of claim 1, further defined as comprising an 18% fibrinogen formulation in combination with riboflavin-5-phosphate.

13. The composition of claim 1, wherein the peptide and the photosensitizer are combined within a single composition.

14. The composition of claim 1, wherein the peptide and the photosensitizer are separate compositions.

15. A composition comprising from about 1% (w/v) to about 50% (w/v) of a biocompatible peptide in solution and in combination with an amount of a flavin photosensitizer capable of producing reactive oxygen species and effective to promote the formation of an adhesive upon photoactivation without more than about 2° C. rise in temperature, the combination intended for use as a tissue adhesive.

16. The composition of claim 15, wherein the peptide is present within a selected tissue and wherein said composition is intended for application to the selected tissue.

17. The composition of claim 16, wherein the peptide composition comprises crystallin lens protein and wherein said composition is intended for application to the eye.

18. A method of using the composition of claim 1 for forming an adhesive connection between tissues, comprising:

(a) providing a composition in accordance with claim 1;
(b) applying the composition to the tissues to be connected to form a tissue adhesive combination; and
(c) applying electromagnetic energy to the tissue adhesive combination in a manner effective to promote the formation of an adhesive connection between the tissues.

19. The method of claim 18, wherein the electromagnetic energy applied has a wavelength of between about 10 nm and about 670 nm.

20. The method of claim 18, wherein the electromagnetic energy is in the form of optical energy.

21. The method of claim 18, wherein the electromagnetic energy is in the form of a monochromatic laser beam.

22. The method of claim 21, wherein the laser beam is generated by an argon laser, a krypton laser, a tunable dye laser, an excimer laser or a diode laser.

23. The method of claim 18, wherein the electromagnetic energy is in the form of a polychromatic energy beam.

24. The method of claim 23, wherein the polychromatic energy beam is generated by a incandescent, fluorescent, xenon or mercury vapor light source.

25. The method of claim 18, wherein the electromagnetic radiation is applied for between about 1 second and about 4 minutes.

26. The method of claim 25, wherein the composition comprises fibrinogen or crystallin lens protein.

27. The method of claim 18, wherein the tissue is located within an animal.

28. The method of claim 27, wherein the animal is a human subject.

29. The method of claim 18, wherein the composition comprises a protein or peptide present within the tissue to be connected.

30. The method of claim 18, wherein the composition is applied as a single composition.

31. The method of claim 18, wherein the composition is applied as separate compositions.

32. The method of claim 18, wherein the composition comprises fibrinogen.

33. The method of claim 18, wherein the composition comprises riboflavin-5-phosphate.

34. The method of claim 33, wherein the composition comprises an 18% fibrinogen formulation in combination with riboflavin-5-phosphate.

* * * * *

UNITED STATES PATENT AND TRADEMARK OFFICE
CERTIFICATE OF CORRECTION

PATENT NO. : 5,552,452
DATED : September 3, 1996
INVENTOR(S) : John Khadern, Toan V. Truong It is certified that error appears in the above-indentified patent and that said Letters Patent is hereby corrected as shown below:

In claim 9, column 19, line 53, delete "claim 4" and insert —claim 7— therefor —.

Signed and Sealed this

Tenth Day of December, 1996

*Attest:*

*Attesting Officer*

BRUCE LEHMAN

*Commissioner of Patents and Trademarks*